United States Patent [19]
Russin

[11] Patent Number: 5,807,276
[45] Date of Patent: Sep. 15, 1998

[54] BIOPSY DEVICE AND METHOD

[76] Inventor: Lincoln David Russin, 440 Westhampton Rd., Northampton, Mass. 01060

[21] Appl. No.: 880,560

[22] Filed: Jun. 23, 1997

Related U.S. Application Data

[63] Continuation of Ser. No. 386,111, Mar. 9, 1995, abandoned.

[51] Int. Cl.[6] ..................................................... A61B 5/00
[52] U.S. Cl. ............................................................. 600/567
[58] Field of Search ........................... 128/749, 751–754; 606/167, 170; 600/562, 564–567

[56] References Cited

U.S. PATENT DOCUMENTS

| | | | |
|---|---|---|---|
| 2,541,542 | 2/1951 | Perez et al. | 128/754 |
| 4,007,732 | 2/1977 | Kvavle et al. | |
| 4,177,797 | 12/1979 | Baylis et al. | 128/754 |
| 4,262,676 | 4/1981 | Jamshidi | 128/754 |
| 4,461,305 | 7/1984 | Cibley . | |
| 4,651,752 | 3/1987 | Fuerst . | |
| 4,682,606 | 7/1987 | DeCaprio | 128/754 |
| 4,691,333 | 9/1987 | Gabriele et al. | |
| 4,727,565 | 2/1988 | Ericson . | |
| 4,821,727 | 4/1989 | Levene et al. | |
| 4,837,795 | 6/1989 | Garrigus . | |
| 4,966,583 | 10/1990 | Debbas . | |
| 5,074,311 | 12/1991 | Hasson . | |
| 5,083,570 | 1/1992 | Mosby . | |
| 5,111,828 | 5/1992 | Kornberg et al. | 128/754 |
| 5,133,360 | 7/1992 | Spears | 128/754 |
| 5,148,813 | 9/1992 | Bucalo . | |
| 5,172,702 | 12/1992 | Leigh et al. | |
| 5,183,463 | 2/1993 | Debbas . | |
| 5,188,118 | 2/1993 | Terwilliger . | |
| 5,267,572 | 12/1993 | Bucalo . | |
| 5,316,014 | 5/1994 | Livingston . | |
| 5,415,169 | 5/1995 | Siczek et al. | |
| 5,445,645 | 8/1995 | Debbas . | |
| 5,452,367 | 9/1995 | Bick et al. | |
| 5,499,989 | 3/1996 | LaBash . | |
| 5,507,298 | 4/1996 | Schramm et al. | |
| 5,526,822 | 6/1996 | Burbank et al. | |
| 5,570,699 | 11/1996 | Kass . | |
| 5,573,008 | 11/1996 | Robinson et al. | |

*Primary Examiner*—Max Hindenburg
*Attorney, Agent, or Firm*—Richard J. Birch

[57] ABSTRACT

A device and method for performing a biopsy on a human breast. The inventive device and method includes a K-wire positionable through a lesion to be removed. A widening incision is made in the breast and permits concentric positioning of a cylindrical cannula to a point above the lesion. The cannula is advanced into the breast about the lesion to cut a cylindrical incision therearound. A snare wire is concentrically positioned over the cannula and tensioned to effect severing of a cylindrical volume of tissue within the cannula for removal from the breast.

9 Claims, 7 Drawing Sheets

BIOPSY DEVICE AND METHOD

This application is a continuation of application Ser. No. 08/386,111 filed on Mar. 9, 1999, now abandoned.

BACKGROUND OF THE INVENTION

1. Field of the Invention

The present invention relates to surgical apparatus and procedures and more particularly pertains to a biopsy device and method for performing a biopsy on a human breast.

2. Description of the Prior Art

Mammography detects small mass lesions and tiny clusters of mircocalcification which are often the earliest indication of breast malignancy. Hook-wire needle localization followed by open surgical biopsy is the standard procedure to remove these lesions, but only a third of the patients actually have cancer. Thus, the majority of women experience a surgical procedure in an operating room, often under general anesthetic, for benign disease.

Mammographic x-rays taken during needle placement enable the radiologist to position the tip of the hook-wire within a few millimeters of the lesion. However, a surgeon performing the biopsy sees only the wire protruding through the skin and has only a general idea of the location of the tip of the wire. Small masses and clusters of mircocalcification in breast tissue are not conspicuous to the unaided eye. With scissors and a scalpel, the surgeon removes a portion of tissue around the tip of the wire. Ideally, the lesion should be excised completely within this portion and surrounded by a zone of normal tissue. An x-ray of the specimen is performed to confirm that the lesion seen on mammography has been removed. Often, however, the lesion is near the margin of the specimen or is incompletely excised. Occasionally, the lesion is not present within the specimen. The surgical procedure must then be repeated at a later date with a second hook-wire localization. Thus, the precision of mammographically-guided hook-wire placement is often not matched by surgical biopsy.

Recently, mammographically-guided "large-core" needle biopsy has been proposed as an alternative to open surgical biopsy. It is performed on a special table with patient prone, and with imaging accomplished by a computerized mammographic machine. Alternatively, it is performed with a stereotactic module added onto a standard mammographic machine. This technique delivers a specimen approximately a millimeter in diameter and ten or twenty millimeters in length and can remove selected microcalcifications within a cluster. Unfortunately, only eighty-five to ninety-five percent of cancer will be accurately diagnosed by "large-core" biopsy because the sample is small and the nests of malignant cells may not be immediately adjacent to the microcalcifications removed in the biopsy. If the cancer is missed, follow-up at six months might show a change which could lead to open surgical biopsy. However, there is a possibility that some patients will receive false assurance from a negative biopsy and their cancers will remain untreated for many months despite early detection on mammography.

Therefore, biopsy of early breast malignancies by current techniques has certain limitations. Open biopsy is imprecise because the surgeon cannot see the lesion, and dissection of the specimen is guided only by the position of the wire in the breast. It involves the expense of a surgical procedure and the possible risk of a general anesthetic. "Large-core" biopsy produces a small tissue sample which could miss the cancer altogether. Further, "large-core" biopsy requires expensive and specialized equipment which is not available in many communities.

Examples of prior art surgical apparatus and procedures for performing biopsies can be found in U.S. Pat. No. 5,056,523; U.S. Pat. No. 5,078,142; U.S. Pat. No. 5,197,482; U.S. Pat. No. 5,060,658, U.S. Pat. No. 5,197,484, and U.S. Pat. No. 5,111,828.

Therefore, it can be appreciated that there exists a continuing need for a new biopsy device and method which can be utilized for performing a complete and accurate biopsy on a human breast. In this regard, the present invention substantially fulfills this need.

SUMMARY OF THE INVENTION

In view of the foregoing disadvantages inherent in the known types of surgical apparatus and procedures now present in the prior art, the present invention provides a new biopsy device and method construction wherein the same can be utilized for performing a complete and accurate biopsy on a human breast. As such, the general purpose of the present invention, which will be described subsequently in greater detail, is to provide a new biopsy device and method apparatus and method which has many of the advantages of the surgical apparatus and procedures mentioned heretofore and many novel features that result in a biopsy device and method which is not anticipated, rendered obvious, suggested, or even implied by any of the prior art surgical apparatus and procedures, either alone or in any combination thereof.

To attain this, the present invention generally comprises a device and method for performing a biopsy on a human breast. The inventive device and method includes a K-wire positionable through a lesion to be removed. A widening incision is made in the breast and permits concentric positioning of a cylindrical cannula to a point above the lesion. The cannula is advanced into the breast about the lesion to cut a cylindrical incision therearound. A snare wire is concentrically positioned over the cannula and tensioned to effect severing of a cylindrical volume of tissue within the cannula for removal from the breast.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new biopsy device and method apparatus and method which has many of the advantages of the surgical apparatus and procedures mentioned heretofore and many novel features that result in a biopsy device and method which is not anticipated, rendered obvious, suggested, or even implied by any of the prior art surgical apparatus and procedures, either alone or in any combination thereof.

It is another object of the present invention to provide a new biopsy device which may be easily and efficiently manufactured and marketed.

It is a further object of the present invention to provide a new biopsy device which is of a durable and reliable construction.

An even further object of the present invention is to provide a new biopsy device which is susceptible of a low cost of manufacture with regard to both materials and labor, and which accordingly is then susceptible of low prices of sale to the consuming public, thereby making such biopsy devices economically available to the buying public.

Still yet another object of the present invention is to provide a new biopsy device and method which provides in the apparatuses and methods of the prior art some of the advantages thereof, while simultaneously overcoming some of the disadvantages normally associated therewith.

Still another object of the present invention is to provide a new biopsy device and method for performing a biopsy on a human breast so as to remove a cylindrical volume of tissue within which a lesion is present.

Yet another object of the present invention is to provide a new biopsy device and method which includes a K-wire positionable through a lesion within a breast, with a widening incision being made in the breast to permit concentric positioning of a cylindrical cannula over the K-wire into a point above the lesion such that the cannula can be advanced into the breast about the lesion to cut a cylindrical incision therearound, and a snare-wire being concentrically positionable over the cannula and tensioned to effect severing of a cylindrical volume of tissue within the cannula for removal from the breast.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
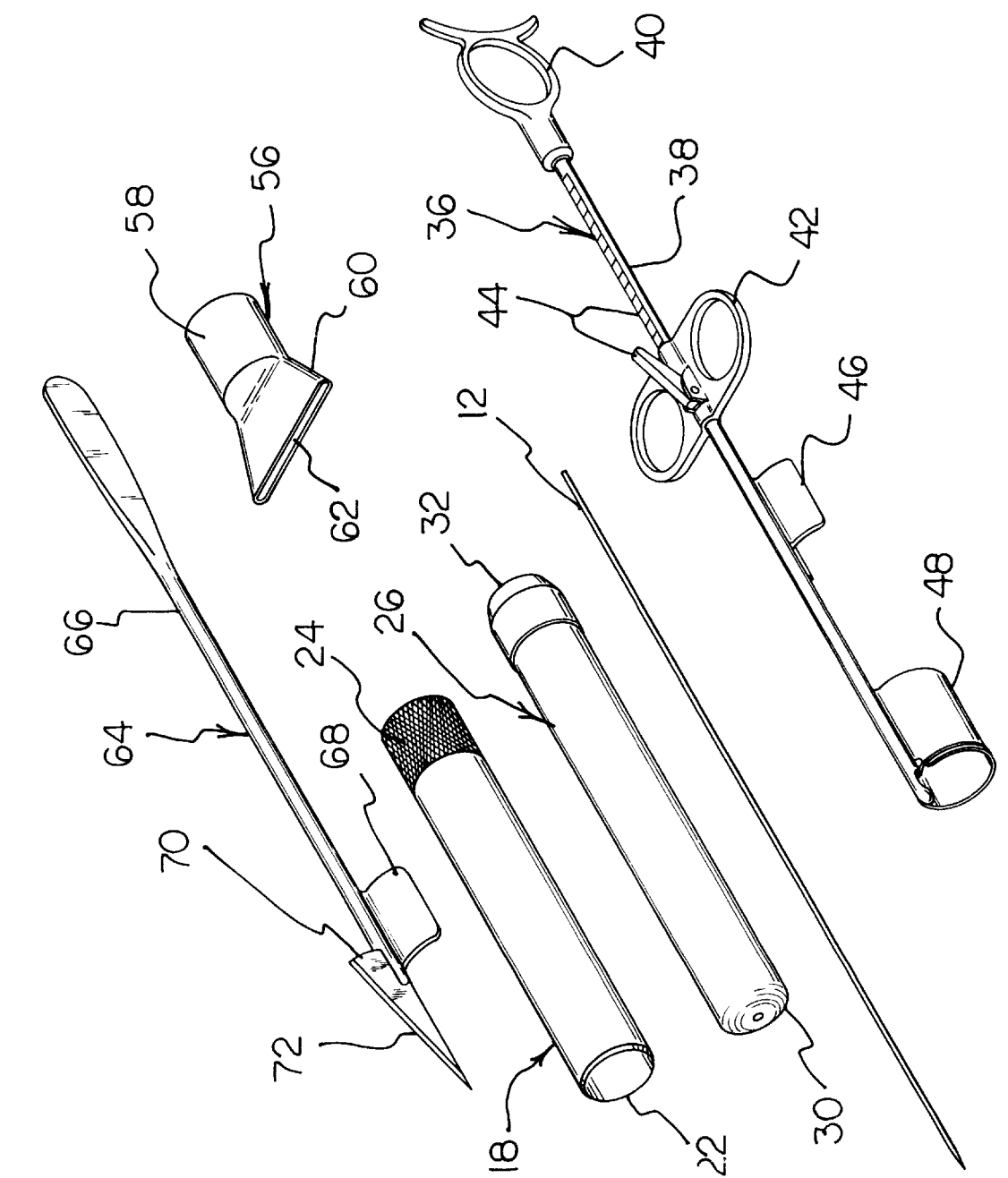
FIG. 1 is an isometric illustration of a plurality instruments according to the present invention.

With reference now to the drawings, and in particular to FIGS. 1–13thereof, a new biopsy device and method embodying the principles and concepts of the present invention and generally designated by the reference numeral 10 will be described.

More specifically, it will be noted that the biopsy device and method 10 comprises a plurality of instruments as illustrated in FIGS. 1 through 5. The instruments include a straight K-wire 12 having a sharpened tip which can positioned through a lesion 14 within a breast 16, as shown in FIG. 6. The straight K-wire 12 can be positioned with repeated mammograms so as to extend through the lesion within the breast as illustrated in FIG. 6 for example.

Figure 2:
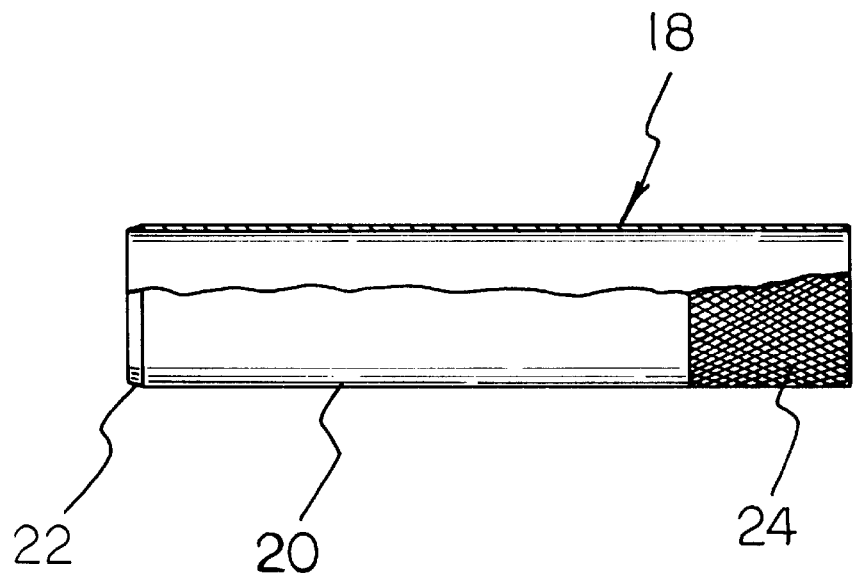
FIG. 2 is a side elevation view, partially in cross section, of a cannula of the invention.

A cannula 18, as best shown in FIG. 2, is comprised of a substantially straight hollow cylinder 20 having a sharpened annular end 22 for cutting tissue, and a textured knurled end 24 for facilitating manual manipulation of the cannula.

Figure 3:
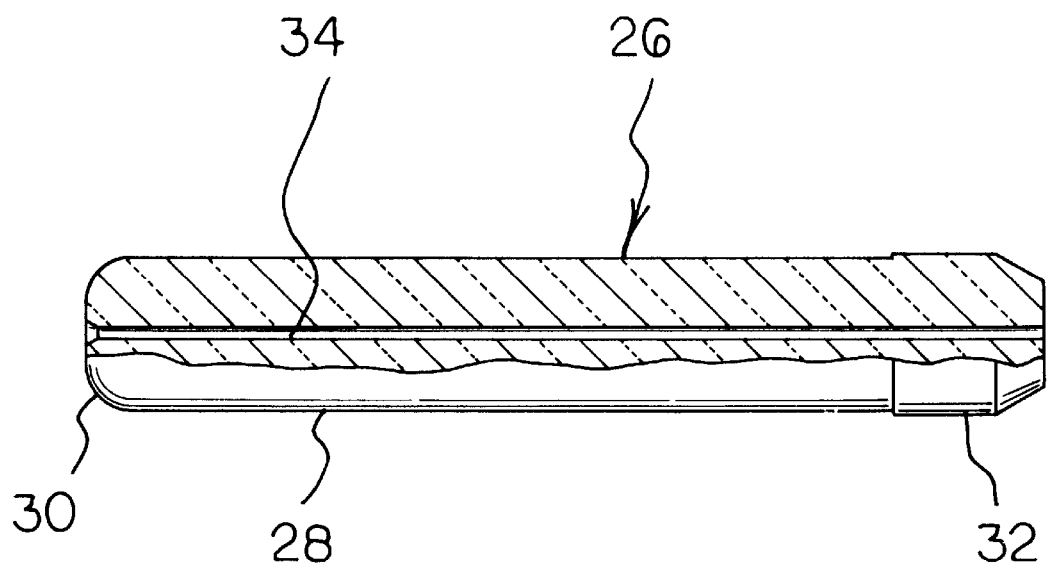
FIG. 3 is a side elevation view, partially in cross section, of an obturator of the invention.

As shown in FIG. 3, an obturator 26 is comprised of a solid cylinder 28 having an outside diameter substantially less than an inside diameter of the hollow cylinder 20 of the cannula 18 so as to facilitate positioning of the obturator within the cannula. The solid cylinder 28 is shaped so as to define a blunt end 30 for permitting non-traumatic positioning of the obturator 26 within a human breast 16. The solid cylinder 28 is further shaped so as to define an enlarged end 32 having an outside diameter substantially greater than an inside diameter of the hollow cylinder 20 of the cannula 18 so as to preclude complete passage of the obturator 26 through the cannula. A cylindrical aperture 34 extends concentrically through the solid cylinder 28 along a longitudinal length and permits passage of the K-wire 12 therethrough. By this structure, the obturator 26 can be positioned within the cannula 18 such that the blunt end 30 of the solid cylinder 28 projects beyond the sharpened annular end 22 for purposes which will subsequently be described in detail.

Figure 4:
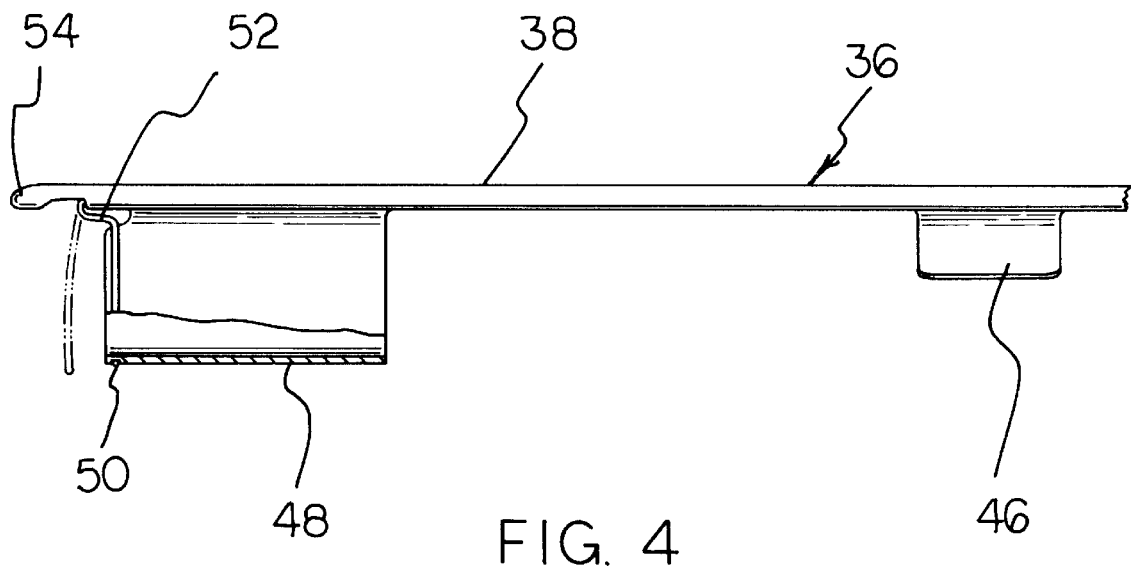
FIG. 4 is a side elevation view, partially in cross section, of a snare.

As best shown in FIGS. 1 and 4, the present invention further includes a snare 36 comprising an at least partially hollow elongated member 38 having a fixed handle 40 at a first end thereof. A sliding handle 42 is mounted about a portion of the elongated member 38 and securable relative thereto by a linear ratchet assembly 44. An arcuate guide plate 46 and a guide cylinder 48 project from the elongated member 38 proximal to a second end thereof and cooperate to facilitate guidance of the elongated member 38 over an exterior of the cannula 18. As clearly shown in FIG. 4, a snare wire 50 projects through the elongated member 38 of the snare 36 and exits therefrom proximal to the second end of the elongated member. The snare wire 50 is formed into a loop which can be drawn into the elongated member 38 to effect severing of a tissue sample. The snare wire 50 is further shaped so as to define an offset portion 52 which permits the snare wire to reside within an annular exterior groove formed along the guide cylinder 48 during insertion of the snare 36 into a human breast 16 to preclude unintentional engagement of the snare wire 50 with surrounding tissue. A blunt end 54 formed at the second end of the elongated member 38 reduces trauma to the breast tissue during insertion of the snare 36 thereinto. By this structure, the snare wire 50 can be retained along an exterior surface of the guide cylinder 48 within the annular groove extending thereabout, with a movement of the sliding handle 42 in a first direction towards the second end of the elongated member 38 effecting removal of the snare wire 50 from the exterior of the guide cylinder 48 into the position illustrated in phantom in FIG. 4. The sliding handle 42 can then be moved in a second direction towards a first end of the elongated member 38 to effect tensioning of the snare wire and reduction of the size of the loop of the snare wire to effect severing of a tissue sample contained within the cannula as will be subsequently described in more detail.

Figure 5:
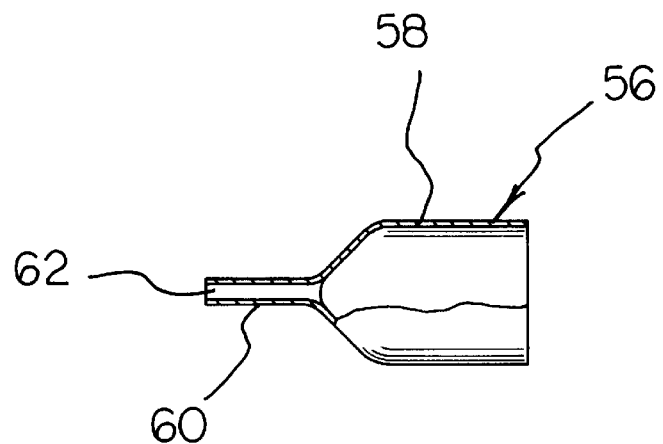
FIG. 5 is a side elevation view, partially in cross section, of an incision guide.
Figure 6:
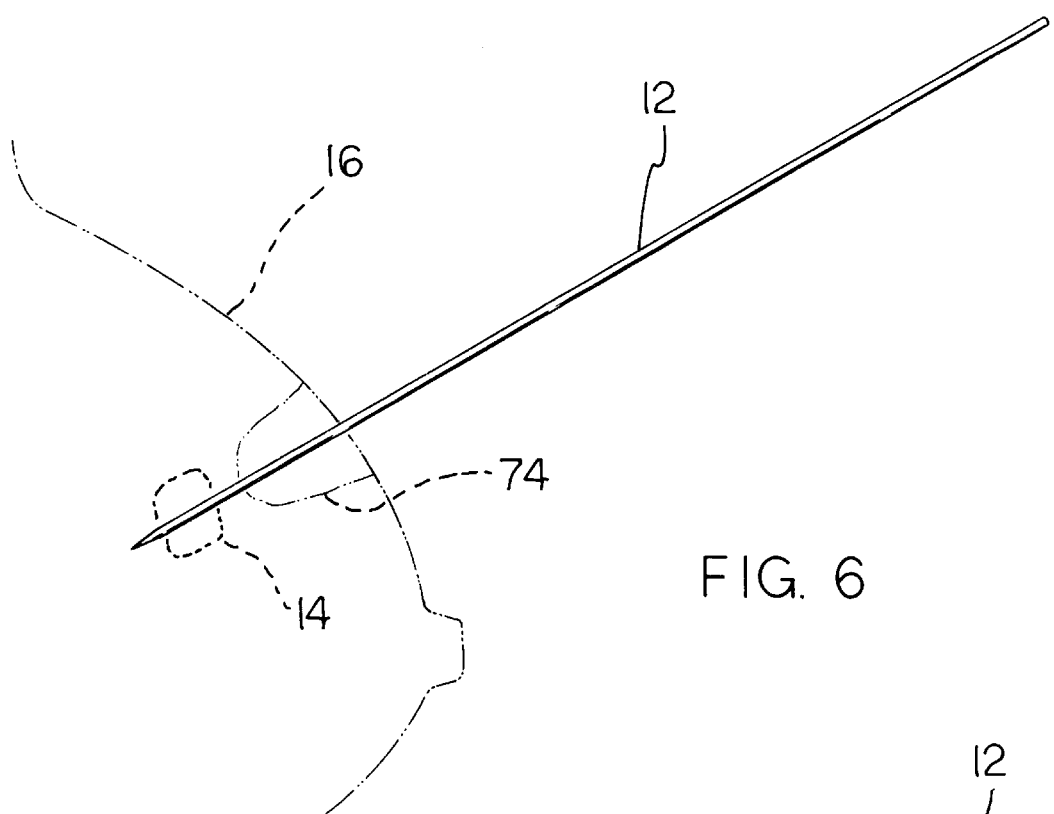
FIG. 6 is an isometric illustration detailing placement of a K-wire through a lesion within a breast.

As shown in FIGS. 1 and 5, an incision guide 56 can be provided to facilitate precise incisions within the breast 16 during a biopsy procedure. The incision guide 56 comprises an incision guide cylinder 58 tapering and integrally continuing into a flattened triangular envelope 60 defining an elongated aperture 62 through which a scalpel or other sharp cutting instrument can be manipulated to effect creation of a linear incision.

The last instrument utilized in the present invention 10 is an orthogonal scalpel 64, as illustrated in FIG. 1, which can be utilized to create an incision oriented substantially orthogonally relative to a tangent line taken along an exterior surface of the cannula 18. The orthogonal scalpel 64 comprises a scalpel handle 66 having a first end shaped for manual manipulation, and a second end from which an arcuate guide member 68 projects. The arcuate guide member is operable to slidably engage an exterior surface of the cannula 18 to facilitate guidance of the orthogonal scalpel 64 during the biopsy method. An angled blade 70 projects from a second end of the scalpel handle 66 and includes a blade edge 72 oriented at an oblique angle relative to a longitudinal axis of the scalpel handle. Preferably, the blade edge 72 extends from a point aligned with the longitudinal axis of the scalpel handle 66 and extends upwardly and angularly therefrom to terminate in a point spaced from the longitudinal axis of the scalpel handle.

A method of performing a biopsy according to the present invention 10 is illustrated in FIGS. 6 through 11. In performing this method, the patient is positioned on her side with the breast in the mammographic grid (CC projection). The lesion is identified on a scout mammogram and the skin over the lesion is sterilized and injected with a local anesthetic.

The K-wire 12 is passed through the center of the lesion using mammographic guidance. In other words, as the K-wire 12 is inserted into the breast 16 mammograms can be repeatedly taken to facilitate identification of the location of the tip of the K-wire 12 relative to the lesion 14 within the breast 16. The breast is then imaged again at a ninety degree angle (MLO projection) and another mammogram is taken to confirm that the K-wire passed through the lesion 14.

A skin incision 74 is then made within the breast 16, with the K-wire 12 being centered along a longitudinal length of the incision 74. Preferably, the incision 74 is of a length of approximately three centimeters. The incision 74 may be created with scissors or a scalpel and preferably extends into the breast along the K-wire to a point of approximately one centimeter above the lesion 14 as seen on additional mammographic exposures. To create the incision 74, the incision guide 56 can be positioned over the K-wire 12, with the K-wire being center within the elongated aperture 62 whereby a scalpel or the like can be passed through the elongated aperture to cut the skin and tissue of the breast 16.

Figure 7:
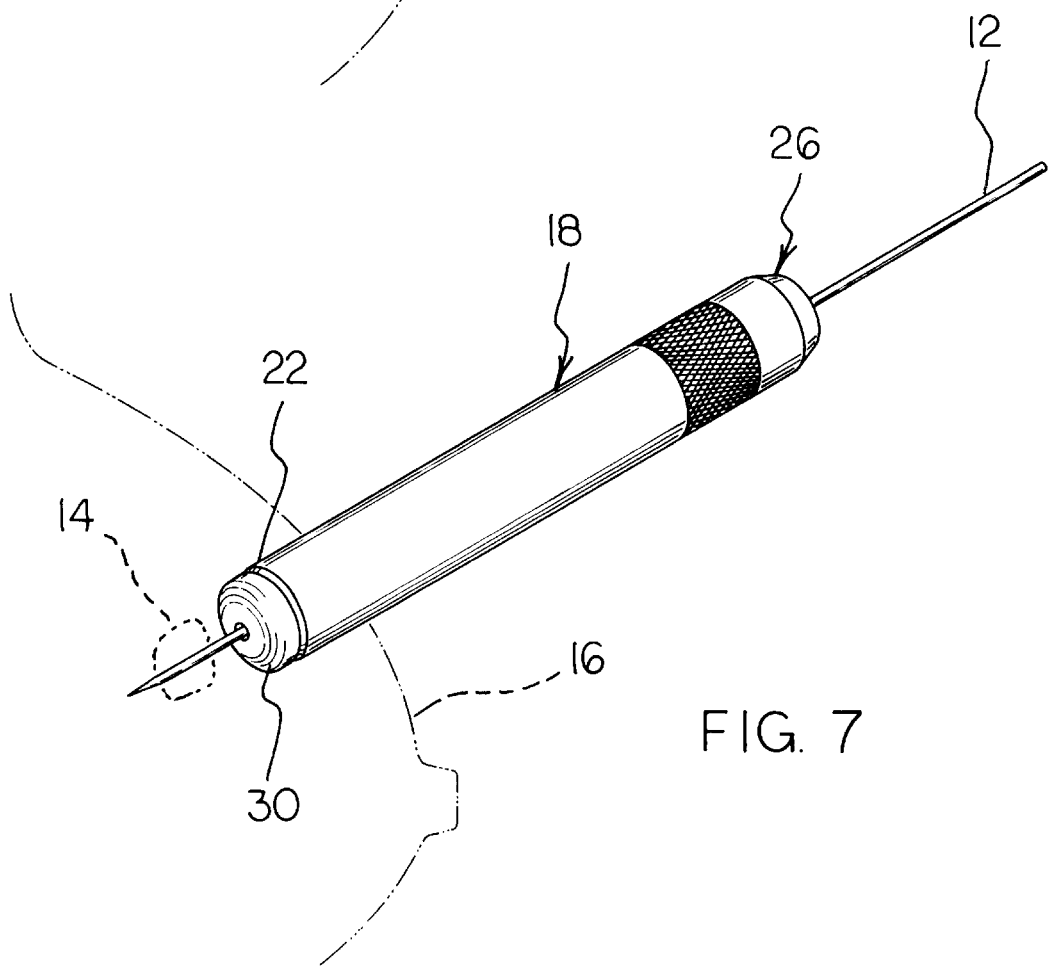
FIG. 7 is an isometric illustration detailing placement of the cannula and obturator concentrically over the K-wire and into the breast.
Figure 8:
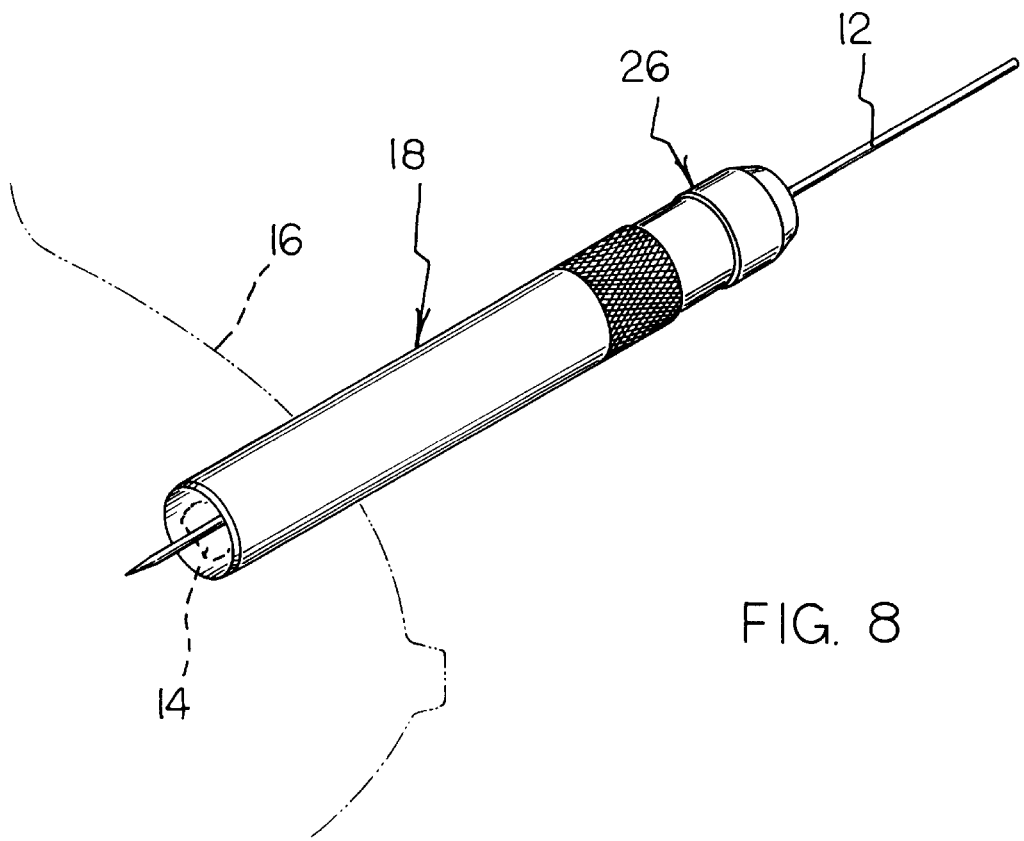
FIG. 8 is an isometric illustration detailing a severing of tissue surrounding the lesion within the breast.

Next, and as shown in FIG. 7, the obturator 26 is concentrically positioned within the cannula 18 such that the blunt end 30 projects beyond the sharpened annular end 22 of the cannula. The obturator 26 with the cannula 18 so concentrically positioned thereabout is inserted into the breast 16 over the K-wire 12. The cannula 18 and obturator 26 assembly is advanced over the K-wire 12 and into the breast through the incision 74 to a point just above the lesion 14. An additional mammogram can be taken to confirm the proper positioning of the cannula 18 just above the lesion. The obturator 26 is then withdrawn approximately three centimeters to expose the sharpened annular edge or end 22 of the cannula. The cannula 18 can then be manipulated into rotary back-and-forth motion and advanced into the breast 16, thereby cutting a cylinder of tissue extending about the lesion 14. Another mammogram can be taken to confirm that the cannula has passed over the lesion 14, such as is shown in FIG. 8.

Figure 9:
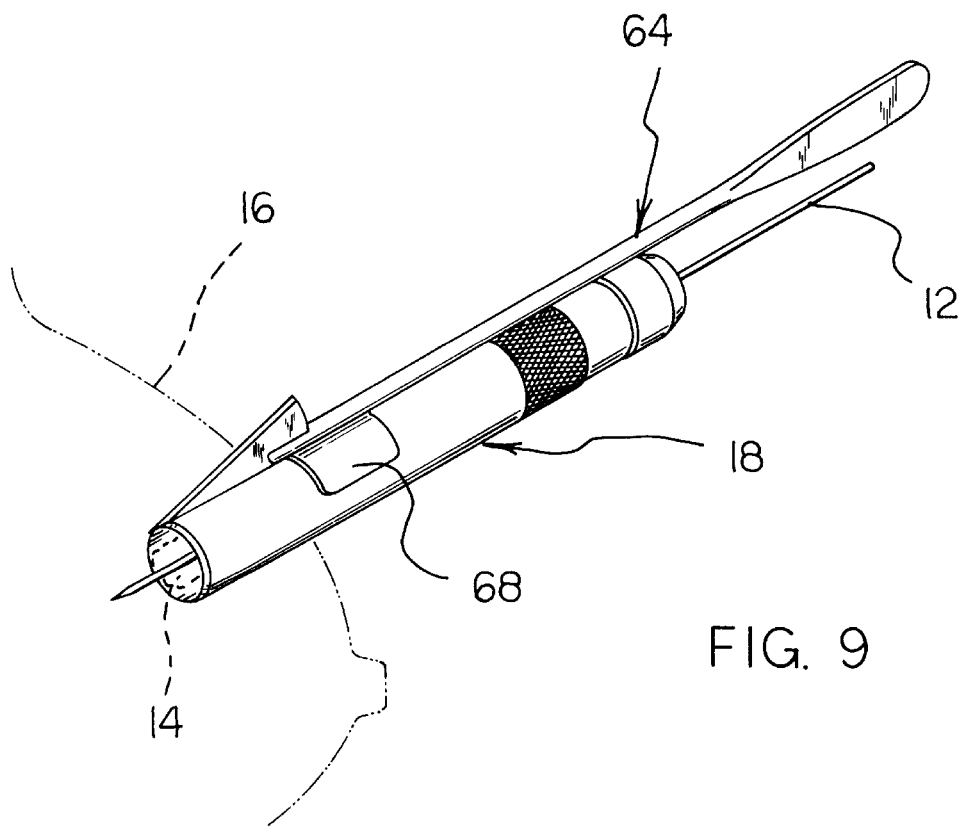
FIG. 9 is an isometric illustration detailing the creation of a relaxing incision through the use of an orthogonal scalpel extending along an exterior of the cannula.

Referring now to FIG. 9, it can be shown that the biopsy method according to the present invention 10 further comprises positioning of the orthogonal scalpel 64 in a parallel orientation relative to the cannula 18 such that the arcuate guide member 68 of the orthogonal scalpel resides along an exterior surface of the cannula. The orthogonal scalpel 64 can be advanced into the breast 16 such that the angled blade 70 creates a relaxing incision extending substantially orthogonally from the cannula 18. The relaxing incision permits entrance of the snare 36 into the breast 16 such as is shown in FIG. 10.

Figure 10:
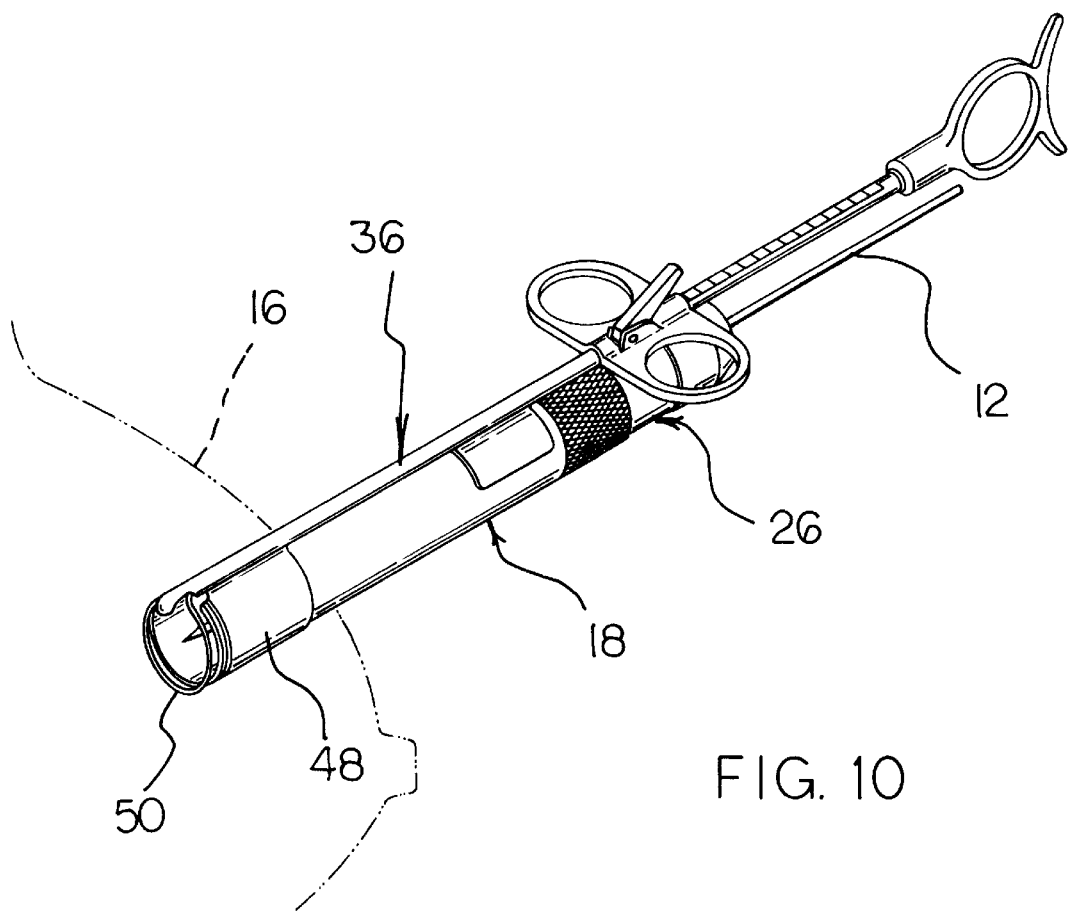
FIG. 10 is an isometric illustration detailing placement of a snare concentrically over the cannula.
Figure 11:
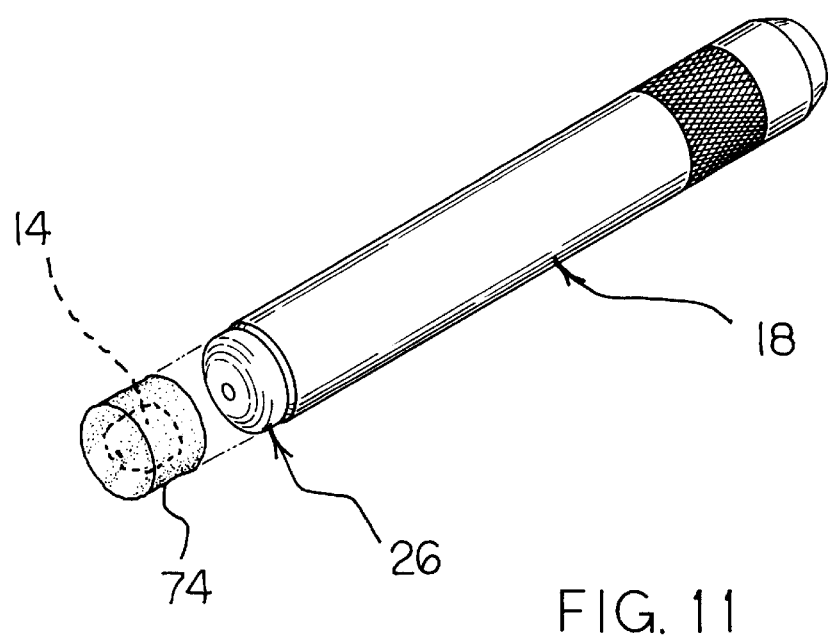
FIG. 11 is an isometric illustration of a cylinder of tissue extruded from the cannula.

With continuing reference to FIG. 10, it can be shown that the snare 36 can be slidably positioned over the cannula 18 and obturator 26 assembly to facilitate positioning of the guide cylinder 48 of the snare 36 over the sharpened annular end 22 of the cannula. The snare wire 50 can then be released from the annular groove in the exterior surface of the guide cylinder and concentrically tightened about the cylinder of tissue 74 to effect severing of the cylinder of tissue from the breast 16. If desired, electrocautery can be applied through the snare wire 50 of the snare 36 to aid in severing of the cylinder of tissue 74. The cannula 18 and obturator 26 assembly containing the cylinder of tissue 74 can then be removed either over the K-wire 12, or alternatively can be removed with the K-wire during concurrent removal of the K-wire from the breast 16. The tissue sample 74 can then be extruded from the cannula 18 through a use of the obturator 26, such as is shown in FIG. 11. A specimen x-ray can be taken to confirm that the lesion 14 is contained within the cylinder of tissue 74. Also, another mammogram can be taken of the breast 16 to confirm that the is no residual abnormal tissue at the biopsy site therewithin. Preferably, a surgical clip is attached to the breast tissue at the biopsy site, again with mammographic guidance to mark the location of the biopsy in case wider excision is indicated based on pathologic evaluation of the specimen 74.

Subsequent to termination of bleeding, the skin of the breast 16 can be sutured in a conventional manner. A small surgical drain can be desirably left in the incision to avoid post-biopsy hematoma.

Although the present invention 10 is particularly useful for effecting the removal of lesions 14 of less than one centimeter in diameter, larger lesions could be removed by increasing a diameter of the cannula 18, or by additional passes of the two centimeter diameter cannula illustrated herein.

Figure 12:
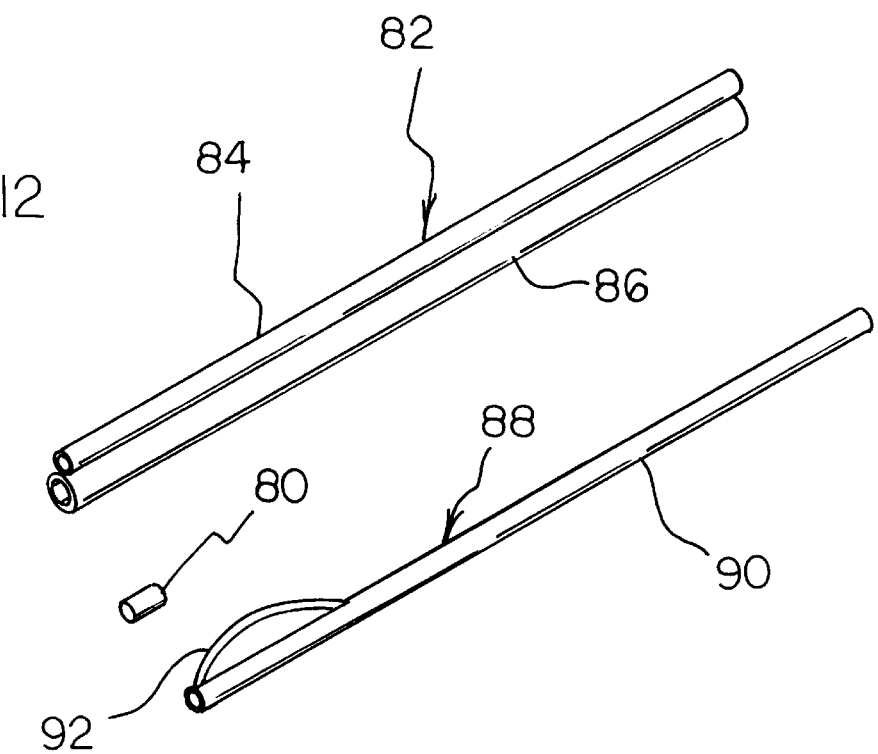
FIG. 12 is an isometric illustration of a further plurality instruments according to the present invention.
Figure 13:
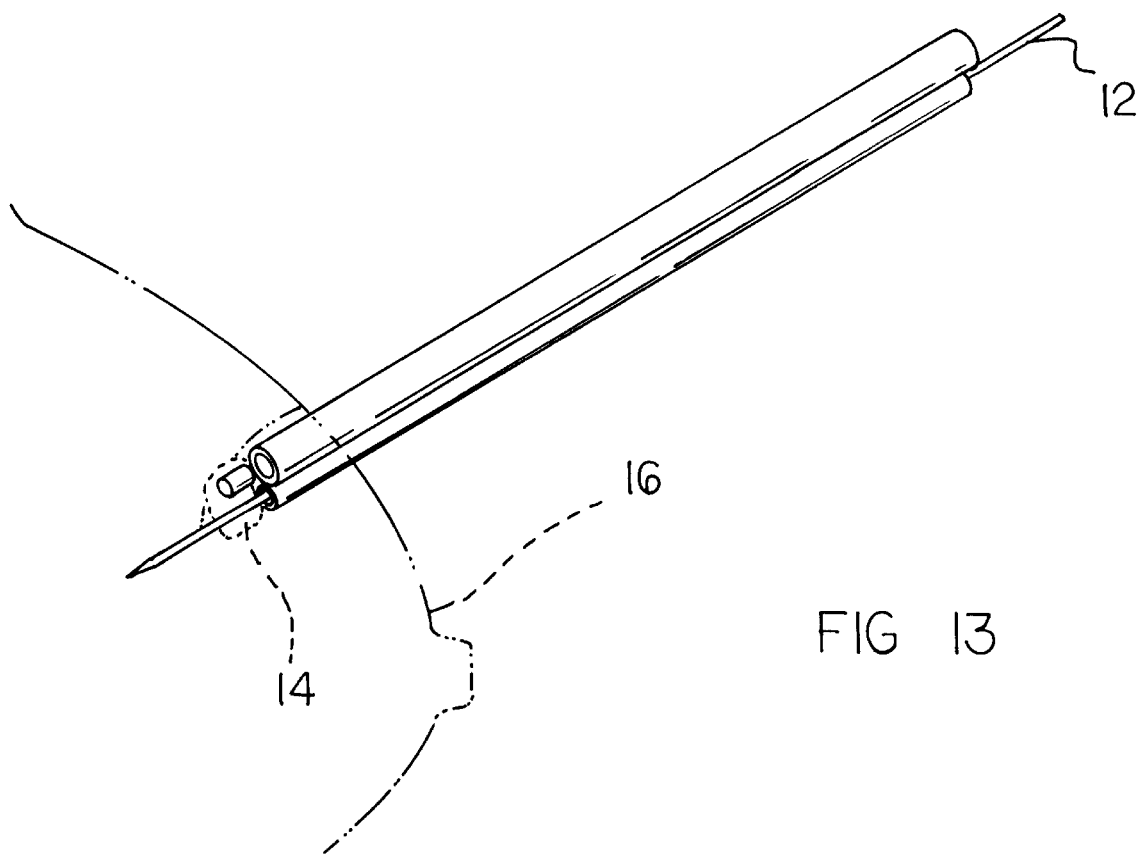
FIG. 13 is an isometric illustration of an insertion of a metal target into the breast.

Referring now to FIGS. 12 and 13, it can be shown that the biopsy device and method according to the present invention may further comprise a metal target 80 which can be identified with fluoroscopic imaging within an operating room. The metal target 80 may comprise a radium seed which exhibits radioactive properties useful in the treatment of carcinomas of the prostate gland. To facilitate placement of the metal target 80 into the breast 16 proximal to the lesion 14, a metal target guide 82 can be provided. The metal target guide 82, as shown in FIG. 12, comprises a K-wire tube 84 which can be concentrically positioned over the K-wire 12 extending through the lesion 14. A metal target tube 86 is coupled to an exterior of the K-wire tube 84 and can slidably receive the metal target 80 for positioning into the breast 16. Although not specifically illustrated, a suitable pushing means, such as a wire or the like, can be utilized to force the metal target 80 into the breast 16 through the metal target tube 86. To facilitate ease of positioning of the metal target guide 82 into the tissue of the breast 16, a K-wire scalpel 88 can be provided to create an incision extending into the breast 16 prior to creation of the larger incision needed for the cannula 18 as described above. The K-wire scalpel 88 comprises a scalpel tube 90 which can be concentrically positioned over the K-wire 12 extending through the lesion 14. A K-wire scalpel blade 92 is coupled to the exterior of the scalpel tube 90 and is oriented so as to extend partially along a longitudinal length thereof. By this structure, the K-wire scalpel 88 can be concentrically positioned over the K-wire 12 extending through the lesion 14 so as to create an incision extending into or proximal to the lesion. The metal target 80 can then be inserted into or proximal to the lesion 14, whereby conventional and readily available fluoroscopic imaging techniques can be utilized to perform the remainder of the biopsy method 10 as described above.

The metal target guide 82 can also be utilized as a stable port for performing a bone biopsy wherein the K-wire is drilled through the cortex of a bone. The target guide 82 can then be advanced into the proximity of the surface of the bone, with a drill being utilized to create a hole in the bone. Repeated passes of a biopsy needle through the metal target tube 86 could be accomplished to obtain ample tissue for biopsy. Current techniques permit only a single passage of a biopsy needle through a hole drilled in a bone. In a similar manner, the target guide 82 can permit the obtaining of multiple samples of tissue from a soft tissue area by simply rotating the K-wire tube 84 about the K-wire 12 to radially position the metal target tube 86 in a desired radial position about the K-wire. Repeated needle biopsies can then be performed about the K-wire 12 as desired by a surgeon.

In use, the biopsy device and method 10 described herein would enable a radiologist or surgeon to remove a cylinder of tissue 74 around a suspected cancer lesion 14 with great precision. The procedure according to the present invention 10 minimizes the risks associated with current surgical biopsy techniques. The device and method 10 are less expensive than conventional techniques generally available, and can be theoretically performed in any mammographic suite. The device and method 10 serves to increase survival rates in as much as early cancers are completed removed with the first biopsy, rather than incompletely removed or only partially sampled. Further, the present system 10 can be utilized to sample tissues other than breast tissues, if so desired.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A biopsy device kit comprising:

a rigid K-wire having a straight sharpened tip;

a substantially straight, hollow cylindrical cannula having a sharpened annular end for cutting tissue;

an obturator concentrically positionable within the cannula, said obturator comprising a solid cylinder having an outside diameter substantially less than an inside diameter of the hollow cylinder of the cannula so as to facilitate positioning of the obturator within the cannula, the solid cylinder being shaped so as to define a blunt end and having a cylindrical aperture extending concentrically through the solid cylinder along a longitudinal length thereof to accommodate the rigid K-wire when it is positioned therein; and, a snare for positioning over the cannula to effect severing of a tissue sample within the cannula.

2. A method of biopsy comprising the steps of:

providing the kit of claim 1;

inserting the rigid K-wire through a center of a lesion within a body of tissue;

creating a skin incision within the body of tissue proximal to the rigid K-wire;

positioning the obturator concentrically within the cannula such that a blunt end thereof projects beyond the sharpened end of the cannula;

positioning the obturator over the rigid K-wire and inserting the cannula and obturator into the body of tissue through the incision; and, advancing the cannula into the body of tissue to cut a volume of tissue extending about the lesion.

3. The method of biopsy of claim 2, and further comprising the step of severing the volume of tissue extending about the lesion from the body of tissue.

4. The method of biopsy of claim 3, wherein the step of severing the volume of tissue extending about the lesion from the body of tissue comprises the steps of:

provinding a snare having a tightenable snare wire;

positioning the snare over the sharpened end of the cannula; and, tightening the snare wire to effect severing of a volume of tissue from the body of tissue.

5. The method of biopsy of claim 3, wherein the step of severing the volume of tissue extending about the lesion from the body of tissue comprises the steps of:

providing an orthogonal scalpel;

positioning the orthogonal scalpel in a parallel orientation relative to the cannula;

advancing the orthogonal scalpel into the body of tissue to create a relaxing incision extending substantially orthogonally from the cannula;

providing a snare having a tightenable snare wire;

positioning the snare over the sharpened end of the cannula;

tightening the snare wire to effect severing of a volume of tissue from the body of tissue.

6. A biopsy device kit comprising:

a rigid K-wire having a straight sharpened tip;

a cannula comprising a substantially straight hollow cylinder having a sharpened annular end for cutting tissue;

an obturator concentrically positionable within the cannula, said obturator comprising a solid cylinder having an outside diameter substantially less than an inside diameter of the hollow cylinder of the cannula so as to facilitate positioning of the obturator within the cannula, the solid cylinder being shaped so as to define a blunt end and a cylindrical aperture extending concentrically through the solid cylinder along a longitudinal length thereof; and, a snare for positioning over the cannula to effect severing of a tissue sample within the cannula, said snare comprising an at least partially hollow elongated member having a fixed handle at a first end thereof and a sliding handle slidably mounted relative to the elongated member, arcuate guide means for guiding the elongated member relative to the cannula, a snare wire coupled to the sliding handle, the snare wire projecting through the elongated member and exiting therefrom proximal to a second end of the elongated member, the snare wire being formed into a loop which can be drawn into the elongated member to effect severing of a tissue sample.

7. The biopsy device kit of claim 6 wherein the guide means includes an annular exterior groove, and further wherein the snare wire is shaped so as to define an offset portion which permits the snare wire to reside within the annular exterior groove during insertion of the snare into tissue to preclude unintentional engagement of the snare wire with surrounding tissue.

8. The biopsy device kit of claim 7 and further comprising an orthogonal scalpel means for creating an incision oriented substantially orthogonally relative to a tangent line taken along an exterior surface of the cannula.

9. The biopsy device kit of claim 8 and further comprising an incision guide means for facilitating precise incisions within tissue during a biopsy procedure.

* * * * *